United States Patent [19]
Wooley et al.

[11] Patent Number: 6,083,500
[45] Date of Patent: Jul. 4, 2000

[54] BIOLOGICAL CONTROL OF FOOD PATHOGENS IN LIVESTOCK

[75] Inventors: Richard E. Wooley; Emmett B. Shotts, Jr., both of Athens, Ga.

[73] Assignee: University of Georgia Research Foundation, Inc., Athens, Ga.

[21] Appl. No.: 08/944,324

[22] Filed: Oct. 6, 1997

[51] Int. Cl.[7] ...................................................... A01N 63/00
[52] U.S. Cl. .................. 424/93.48; 435/252.33; 435/252.1; 435/172.3
[58] Field of Search ...................... 424/93.48; 435/252.1, 435/172.3, 252.33

[56] References Cited

U.S. PATENT DOCUMENTS 5,302,388  4/1994  Doyle et al. .......................... 424/93 C

OTHER PUBLICATIONS

Kolter, R. and Moreno, F. (1991) "Introduction to the microcin session" *Bacteriocins, Microcins and Lantibiotics*, R. James et al. eds., Springer–Verlag, Berlin, http://www vet.uga.edu/mmb/lee/microcin.htm.

Kolter, R. et al. (1992) "Genetics of Ribosomally Synthesized Peptide Antibiotics," *Ann. Rev. Microbiol.* 46:141–163.

Moreno, F. et al. (1995) *Biotechnology*, Series 28 Genetics and Biochemistry of Antibiotics Production, Ch. 11, "Microcins," Pp. 307–321.

O'Brien, G.J. (1994) "Colicin 24, a new plasmid–borne colicin from a uropathogenic strain of *Escherichia coli*-"*Plasmid* 31:288–296.

Pugsley, A.P. (1984) "The ins and outs of colicins. Part I: Production, and translocation across membranes," *Microbiol. Sci.* 1:168–175.

*Primary Examiner*—Irene Marx
*Attorney, Agent, or Firm*—Greenlee Winner and Sullivan, PC

[57] ABSTRACT

The invention includes novel strains of *E. coli* and methods for treating livestock with strains of the invention to inhibit growth of *S. typhimurium* as well as other pathogenic enterobacteria, such as *E. coli* 0157:H7, in the intestinal tract of treated animals. By inhibiting growth of such contaminant pathogenic organisms in the intestinal tract of treated animals, the number of such organisms living in the animals, or excreted into the environment, is reduced or eliminated. The potential for re-introduction and for contamination of meat and other products is concomitantly reduced or eliminated.

1 Claim, 3 Drawing Sheets

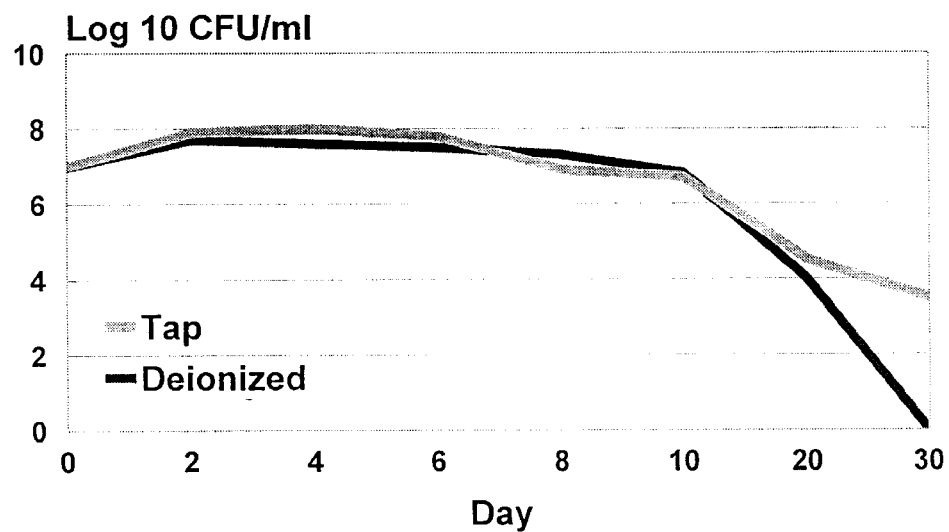

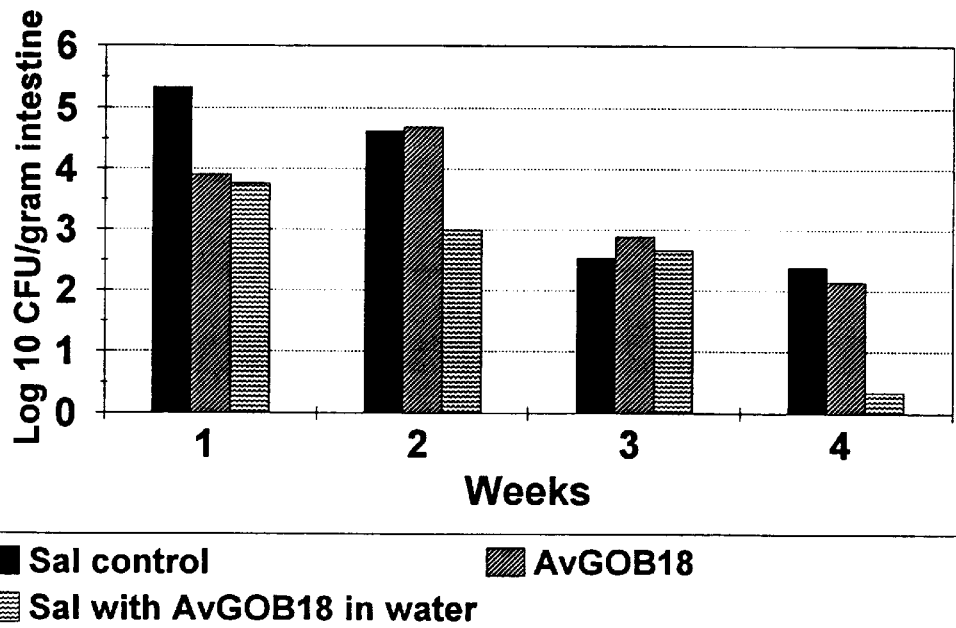

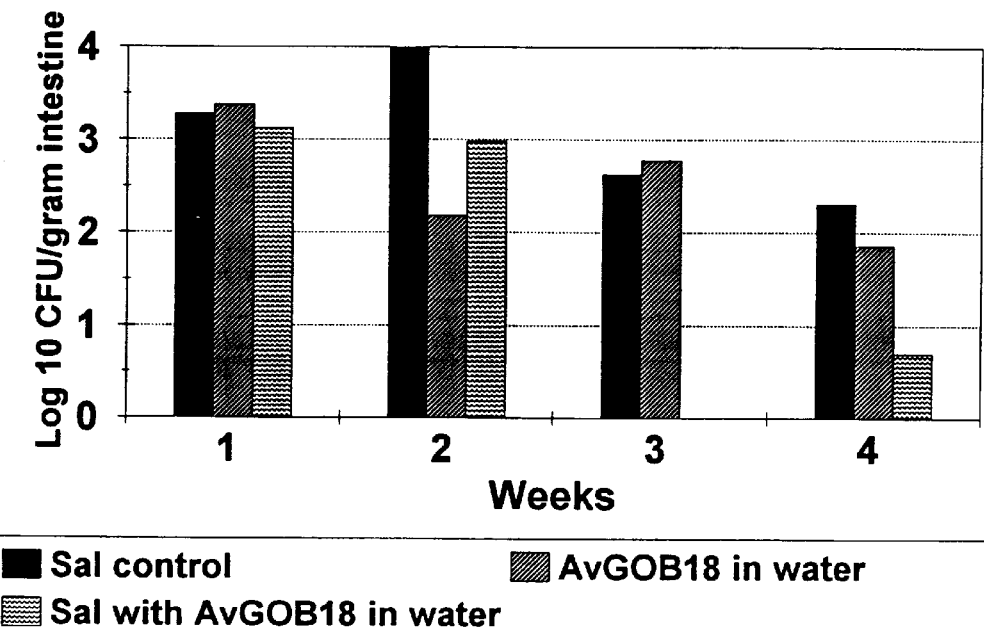

BIOLOGICAL CONTROL OF FOOD PATHOGENS IN LIVESTOCK

CROSS REFERENCE TO RELATED APPLICATIONS

Not applicable.

ACKNOWLEDGEMENT OF FEDERAL RESEARCH SUPPORT

Not applicable.

BACKGROUND OF THE INVENTION

Sporadic outbreaks of illness resulting from microbial contamination of meat and poultry products are a continuing source of medical and public health concern. *Salmonella typhimurium* is a frequent contaminant of poultry, causing severe gastroenteritis which is usually brief and limited to the gastrointestinal tract, but can be more severe in children and the aged. *S. typhimurium* is the most frequently isolated serotype of Salmonella in the United States; however, related serotypes include *S. typhi* which causes typhoid fever and *S. paratyphi* which causes a milder disease, paratyphoid fever. *E. coli* 0157:H7 is another contaminant of livestock that has recently become a serious public health threat. *E. coli* 0157:H7 causes severe hemorrhagic diarrhea and renal disease which can be fatal. Due to the increased incidence of disease from contaminated meat and poultry products, a need has arisen to augment the standard public health measures of control. Such measures are typically applied during processing and packaging, not during growth and rearing of animals for market.

Biological control of pathogen contamination of birds and animals grown for food has rarely been described. Doyle et al., U.S. Pat. No. 5,302,388 described microorganisms capable of preventing *Campylobacter jejuni* colonization of poultry. The microorganisms were selected on the basis of their ability to interfere with specific colonization requirements of *C. jejuni*. Such an approach is not applicable to organisms such as *S. typhimurium* or *E. coli* 0157:H7, since these do not necessarily colonize the host animal, but are simply part of the intestinal flora, where they are able to find nutrients and to multiply.

Bacteriocin is a generic term applied to any of a set of proteinaceous antimicrobial agents produced by certain bacterial strains. Colicin is the term specifically applied to certain bacteriocins produced by *E. coli*. The colicins have been subject to most bacteriocin-related research, although such research has not been extensive. The term microcin has been used in the literature with varying definitions, depending upon the author.

The term microcin is sometimes applied to antibiotic substances produced by diverse strains of Enterobacteriaceae able to pass through dialysis membranes having a molecular weight cut-off of about 10,000 daltons and produced during stationary phase culture. [Moreno, F., et al. (1995) in Biotechnology Series 28, Genetics and Biochemistry of Antibiotics Production, pp.307–321, Butterworth-Heineman Ltd., London]. The bacteriocins have been studied as possible means for strain typing, as possible virulence factors and for the mechanism of their toxicity. The genes for most bacteriocins are carried on plasmids which encode the structural gene, post-translational processing genes and an immunity gene that confers immunity to the cell producing the toxin. There is no clear-cut evidence that production of a bacteriocin confers a selective advantage in the microbial environment. Various assays of natural enterobacterial populations have shown that between 30%–50% are $Col^+$ (capable of producing a colicin). Many colicins are expressed only in response to induction, the inducing agent being typically a DNA damaging agent such as UV light or mitomycin C. Microcins are usually naturally produced during stationary phase existence. Attempts to use bacteriocins as antibiotics or bacteriocin-producing strains as biocontrol agents have generally not been successful. For reviews, see *Bacteriocins, Microcins and Lantibiotics*, R. James et al. eds., Springer-Verlag, Berlin, 1991; Kolter R. et al. (1992) Ann.Rev. Microbiol. 36:125–144; Pegsley, A. P. (1984) Microbiol. Sci. 1:203–205; Moreno F. et al., supra.

O'Brien et al. (1994) Plasmid 31:288–296 reported characterization of *E. coli* strain 2424, isolated from a human patient with pyelonephritis. *E. coli* 2424 was found to produce a previously undescribed colicin, designated colicin 24. Colicin 24 was found to have bactericidal activity on agar plates against various *E. coli* test strains and against *S. typhimurium*. The molecular weight, estimated by SDS-PAGE, was approximately 37.2 Kda. The plasmid responsible for production of col 24 was isolated and the essential genes for col $24^+$ phenotype were transferred to pBR322 to produce a 29.15 kb plasmid, pGOB34, and to pUC18 to produce two 11.39 kb plasmids, pGOB342 and pGOB420, all of which conferred colicin 24 production on host strains transformed by the respective plasmids. The colicin 24 determinants including host immunity appeared to be located on a 8.7 kb Eco RI fragment.

SUMMARY OF THE INVENTION

The invention includes novel strains of *E. coli* and methods for treating livestock with strains of the invention to inhibit growth of *S. typhimurium* as well as other pathogenic enterobacteria, such as *E. coli* 0157:H7, in the intestinal tract of treated animals. By inhibiting growth of such contaminant pathogenic organisms in the intestinal tract of treated animals, the number of such organisms living in the animals, or excreted into the environment, is reduced or eliminated. The potential for re-introduction and for contamination of meat and other products is concomitantly reduced or eliminated.

The microorganisms of the invention are generated by transforming a suitable, non-pathogenic host with a non-transmissible plasmid carrying genetic determinants for microcin 24. Microcin 24 is the same as "colicin 24" (O'Brien et al. supra). However, because induction is not required for its production, the term "microcin 24" abbreviated as "Mcc24" is preferred. The host organism can be any enteric bacteria, preferably *E. coli*, of a strain compatible with and non-pathogenic to, the intended host. The plasmid can be any non-transmissible plasmid capable of replication and expression in the chosen host. The invention is exemplified by an avian *E. coli* strain, transformed with plasmid pGOB18, a plasmid having a 4.2 kb fragment carrying microcin 24 determinants inserted into pBR322. By specifying a non-transmissible plasmid, the possibility of plasmid transfer to the target organism thereby conferring Mcc24 immunity to the target strain is eliminated. Suitable target strains (those whose reduction or removal from the animal is desired) are those susceptible to Mcc24. These include, but are not limited to, *S. typhimurium* and *E. coli* 0157:H7.

Animals are treated by simply causing them to ingest a microorganism of the invention, by any convenient means. Such means include adding the microorganisms to the animals' drinking water, or to their feed, or by direct oral insertion.

The invention is exemplified by treatment of poultry with AvGOB18, an avian E. coli (Mcc24+) administered in drinking water. Significant reduction (about 1000-fold) of S. typhimurium was observed in treated birds.

BRIEF DESCRIPTION OF THE DRAWINGS

FIG. 1—Survival of E. coli AvGOB18 in sterile deionized tap water.

FIG. 2—Results of Bird Studies # 1.

FIG. 3—Results of Bird Studies # 2.

DETAILED DESCRIPTION OF THE INVENTION

The following terms are used herein as defined.

Host organism is used to denote an enteric bacteria strain which can be transformed with a plasmid. Various host organism strains are employed in the invention. Strain choice depends on suitability for transfer to the kind of animal to be treated. Thus, avian E. coli is a suitable host organism for administration to poultry, while bovine strains are suitable for administration to cattle. The host organism chosen can be a natural isolate or it can be genetically altered, for example to carry a marker to permit identification, re-isolation or enumeration after having been administered to an animal. Preferably the host organism is non-pathogenic to the intended recipient animals.

Microcin 24 (also abbreviated Mcc24) is the term given to the bactericidal substance first characterized by O'Brien et al, supra, who called it "colicin 24."

The genetic determinants for Mcc24 production include all genes necessary to convey Mcc24+ phenotype to a host organism. The Mcc+ phenotype includes production of Mcc24 as measured by toxicity to a susceptible test organism, such as S. typhimurium, and also includes immunity to Mcc24.

Mcc24 is produced at least during stationary phase or periods of slow growth by Mcc+ cells. As shown herein, an avian E. coli transformed to produce Mcc24, AvGOB18, remained viable and capable of toxin production in water for 30 days. Chickens provided with drinking water inoculated with AvGOB18 had substantially reduced S. typhimurium counts in their intestinal tracts, compared to controls.

While administration of Mcc+cells to an animal has been shown to reduce the count of Mcc-sensitive bacteria including such pathogens as S. typhimurium and E. coli 0157, in the animal's intestinal tract, reduction can also be accomplished by administering Mcc24 itself. Culture supernatants or filtrates can be used as a source of Mcc24, either as is, concentrated or diluted as necessary to provide an effective dose. However, administering an Mcc+ microorganism is preferred since the latter are likely to be concentrated in the vicinity of the target organisms and to continue to produce Mcc24 as long as the host organism remains viable in the animal.

The terms "target organism" and "contaminant organism" are used interchangably to denote any undesired organism whose presence in or on animal tissues or animal products is undesirable. Any contaminant microorganism pathogenic to humans can be substantially reduced or eliminated from livestock species by administering a microorganism of the invention, provided the contaminant is susceptible to Mcc24. Testing for sensitivity to Mcc24 can be readily conducted by a plate assay, as described herein. An Mcc24+ bacterial culture spotted onto a lawn of the microorganism to be tested yields a zone of clearing, or reduced turbidity in the lawn around the Mcc24+ colony after incubation, if the microorganism of the lawn is susceptible to Mcc24. Susceptible organisms include many E. coli strains, including the pathogenic 0157:H7, as well as S. typhimurium.

Animals can be treated to prevent, reduce or eliminate a pathogenic contaminant by administering cells of a Mcc24+ strain into the animals' intestinal tract. Oral administration is most convenient. The Mcc24+ microorganism can be added to drinking water or to feed, or provided in pellet, capsule or paste form for direct oral administration. The host organism need not be able to colonize the animals' intestinal tract. By administering the Mcc24+ microorganism in feed or drinking water, the treated animal continually receives a fresh dose of the Mcc24+ organism. Continuous administration is preferred because it prevents re-infection by the contaminant from the environment.

Organisms of the invention can be administered as live, metabolizing cells, or in dormant or freeze-dried form. Live metabolizing cells are preferred. The exemplified strains readily survive for at least 30 days in drinking water. Such strains are conveniently administered by simply diluting them in the animals' drinking water. The organisms can also be administered by other means known in the art, such as sprayed onto feed or mixed with a feed additive, combined with nutrients, inert carrier materials, preservatives, excipients, micro-encapsulation media and the like, all as known in the art. Alternatively the Mcc24+ microorganisms can be formulated into a paste extrudable into the mouth similar to, or even combined with other medications, such as worming paste. The microorganisms can also be delivered in capsule or gel form. Compositions which contain live microorganisms should not contain any diluent, solvent or preservative that is deleterious to the viability of the microorganism, as will be understood in the art. Components of a composition can be readily tested for their effect on viability, without undue experimentation, using standard methods known in the art.

The determinants of the Mcc24+ phenotype include a gene(s) that confers Mcc24 immunity to the host cell. Providing the Mcc24 determinants on a non-transmissible plasmid, minimnizes the likelihood of immunity transfer to other strains in the animal gut.

Experimental details are set forth in the following examples:

Materials and Methods

Bacterial Strains. The test organisms include recipient Escherichia coli laboratory strains MC4100, HB101 and SK8203; and wildtype avian E. coli strains Av and V-2 [Wooley, R. E. et al. (1996) Avian Dis. 40:533–539; Wooley, R. E. et al. (1994) Avian Dis. 38:127–134; Wooley, R. E. et al. (1992) Avian Dis. 36:348–352.] Donor, exclusion strain, and challenge isolates include avian E. coli strains V-2, [Wooley, R. E. et al. (1992) Avian Dis. 36:348–352] mutant E. coli strain AvGOB18, and Salmonella typhimurium strain 1769. Other test organisms included: 5 isolates of avian E. coli (Av, V-1, V-2, V-3, V-4) (13) Escherichia coli O157:H7 (7 strains), Salmonella typhimurium, S. enteriditis, S. Heidelberg, S. infantis, S. typhimurium (C), S. kentucky, and S. senftenberg, Listeria monocytogenes F7219 (1/2A), F4022 (4B), and H0437 (untypable); and Campylobacter jejuni (field strain isolated from broiler chickens).

Plasmid. pGOB18 (Mcc24, Microcin 24, Ap$^r$) with structural, transport and immunity genes cloned into pBR322.

Antibiotic resistance profiles. Antibiotic-resistance profiles of the test organisms were determined by the disc diffusion method [Blair, J. E. et al. (1970) Manual of Clinical Microbiology, American Society of Microbiology, Williams and Wilkins, Baltimore, pp. 307; Carter, G. R. (1973) Diagnostic Procedures in Veterinary Microbiology 2nd ed. Charles C. Thomas, Springfield, Ill. pp. 3799–384]. Antibiotics tested included gentamicin (Gm), streptomycin (St), kanamycin (Kn), ampicillin (Ap), chloramphenicol (Cm), nalidixic acid (Na), tetracycline (Tc), sulfisoxazole (Su), sarafloxacin (Srf), enrofloxacin (Eno), bacitracin (B), and neomycin (N).

Media with and without selective antibiotics included: MacConkey and XLT4 agar for the isolation of *E. coli* mutants and *Salmonella typhimurium* strain 1769; Mueller Hinton agar for the determination of antibiotic resistance patterns; nutrient agar for the colicin sensitivity assay; and brain heart infusion broth for propagation of the bacterial strains.

Plasmid isolation and agarose gel electrophoresis. Plasmid DNA was isolated and purified by the method of Bimboim and Doly [Bimboim and Doly, (1979) *Nucleic Acids Res.* 7:1513–1523] from overnight Brain Heart infusion (BHI) broth cultures. Samples of 25 μl of plasmid DNA were loaded into wells of a 0.7% agarose gel and run at 75 volts for 4 hours on a horizontal electrophoresis apparatus. Gels were stained with ethidium bromide, visualized on an ultraviolet transilluminator, and photographed [Simmons, K. W. et al. (1988) *Appl Environ. Microbiol.* 54:760–767].

Transformation. Avian *Escherichia coli* strain Av was made competent and transformed with pGOB18 using the Gene Pulser Transfection Apparatus and Pulse Controller (Bio-Rad Laboratories, Richmond, Calif.) set at 25 μF., 200Ω, and 2.5 kV [Summers and Withers (1990) *Nucleic Acids Res.* 18:2192]. The mutant was designated *E. coli* AvGOB18. Initial selection of mutants was done on the basis of acquisition of resistance to Ap by incorporating this antibiotic into MacConkey agar plates at a concentration of 50 μg/ml. Transformants were colony-purified three times on selective media before being studied further.

Bacterial matings and selection of transconjugants. Transfer of plasmid pGOB18 was attempted by mixing 0.2 ml of exponentially grown donor cells (*E. coli* AvGOB18) with 1.8 ml of an overnight culture of recipient *E. coli* strains MC4100, HB101, and SK8203 [Simmons et al. (1988) supra; Wooley et al (1992) supra] in Penn Assay broth. Mixtures were incubated at 37 C. for 18 hours. Transconjugants were selected on MacConkey agar plates containing a donor-inhibiting and a recipient-inhibiting concentration of antibiotic. Samples from the selector plates were picked and identified by their antibiotic-resistance patterns and plasmid profiles. Frequencies of transconjugants are expressed relative to the number of donor cells in the mating mixture [Simmons et al. (1988) supra; Wooley et al (1992) supra]. *Escherichia coli* strain V-2 was used as a positive conjugative control.

Colicin-like activity. Colicin-production was tested by overlaying chloroform-killed colonies of the test organisms with a colicin-sensitive *E. coli* K-12 (ATCC 23559; American Type Culture Collection, Rockville, Md.), *Salmonella typhimurium* 1769, or other indicator organisms. Plates were incubated at 37 C. for 18 hours, then observed for growth inhibition [Fredericq, P. (1957) *Microbiol.* 11:7–22; Wooley, R. E. et al (1994) *Avian Dis.* 38:141–145; Wooley, R. E. et al. (1993) *Avian Dis.* 37:1092–1096].

Water survival. *Escherichia coli* AvGOB18 was inoculated into sterile tap and deionized water. Mixtures were incubated at 25 C. and 37 C. for 30 days. Samples were taken on day-0 and every 3 days for 30 days. Titers of the mutants reisolated from the water and their inhibitory activity on *S. typhimurium* 1769 was determined.

Type F1 fimbriae and motility. Mannose-sensitive hemagglutination (the presence of type F1 fimbriae) was determined by the agglutination of yeast cells [Korhonen, T. K. (1979) *FEMS Microbiology Letters* 6:421–425]. Brain-heart infusion cultures of the test organisms were incubated statically in air, with subcultures every 48 hours for six transfers before testing. Combinations of 50 μl of bacterial cultures and 1% (w/v) yeast suspension were mixed in a 96-well round-bottomed microliter plate and incubated at room temperature of 2 hours before recording results [Korhonen, T. K. (1979) supra]. The yeast cells consisted of Baker's yeast (Fleischmann's yeast) washed three times in PBS and diluted to 1% (w/v) in PBS containing 0.5% (w/v) formaldehyde [Smyth, C. J. (1988) In: Immunochemical and molecular genetic analysis of bacterial pathogens. P. Owens and T. J. Foster, eds. Elsevier Science Publishers, New York, pp223–244]. Motility was determined by stab inoculation of Motility Test Media (Difco Laboratories, Detroit, Mich.), followed by overnight incubation at 37 C.

In vivo studies.

I. Bird study #1 in Horsfal units.
Groups: 30 birds per group
Oral inoculation with *Salmonella typhimurium* 1769 into four-day-old chicks.
1. Oral inoculum consisted of 150 μl of overnight BHI culture, $Log_{10}$ 8.18 (1.5 × $10^8$ CFU).
2. Oral inoculation with 100 μl *E. coli* AvGOB18 on:
   Day-0, $Log_{10}$ 7.78 (6 × $10^7$ CFU).
   Day-2, $Log_{10}$ 7.74 (5.5 × $10^7$ CFU).
3. Oral inoculation with 100 μl *E. coli* AvGOB18 on:
   Day-0, $Log_{10}$ 7.78 (6 × $10^7$ CFU).
   Day-2, $Log_{10}$ 7.74 (5.5 × $10^7$ CFU).
   Day-4, 150 μl *Salmonella typhimunum* 1769, oral, $Log_{10}$ 8.18, 1.5 × $10^8$ CFU.
4. Day-0, continual administration of *E. coli* AvGOB18 in water, 6 × $10^6$ CFU/ml water, 1:100 dilution of overnight BHI culture, $Log_{10}$ 6.78. Titers in water: ≈ $10^6$ CFU/ml water.
   Day-4, 150 μl *Salmonella typhimurium* 1769, oral, $Log_{10}$ 8.18, 1.5 × $10^8$ CFU.
   Samples of ceca, lower small intestine, and colon were taken for culture on weeks 1, 2, 3, and 4. Five birds per group.
II. Bird study #2 in floor pens.
Groups: 30 birds per group
1. Oral inoculation with *Salmonella typhimurium* 1769 into chicks on day-4 and day-10, -continued In vivo studies.

with 150 μl of overnight BHI culture, ≈ $Log_{10}$ 8.00.
2. Day-0, continual administration of *E. coli* AvGOB18 in water, $1 \times 10^6$ CFU/ml water, 1:100 dilution, ≈ $Log_{10}$ 6.00.
Days-4 and 10, 150 μl *Salmonella typhimurium* 1769, oral, ≈ $Log_{10}$ 8.00.
Samples of ceca, lower small intestine, and colon were taken for culture on weeks 1, 2, 3, and 4. Five birds per group.

Results

Antibiotic profiles. The antibiotic resistance profiles of the test organisms are shown in Table 1.

TABLE 1

Antibiotic resistance profiles or organisms used in study

|  | Ap | Cm | Kn | Na | St | Su | Tc | Eno | N | Srf | B |
|---|---|---|---|---|---|---|---|---|---|---|---|
| Av | S | S | S | R | S | S | S | R | I | R | R |
| V-2 | S | S | S | S | R | R | R | — | — | — | — |
| AvGOB18 | R | S | S | R | S | S | S | R | I | R | R |
| MC4100 + GOB18 | R | S | S | S | R | S | S | S | I | I | R |
| HB101 | S | S | S | R | S | S | S | — | — | — | — |
| MC4100 | S | S | S | S | R | S | S | S | I | I | R |
| pSK8203 | S | S | R | R | S | S | R | — | — | — | — |
| v-2 + pSK8203 | S | S | R | R | R | S | R | — | — | — | — |

R = resistant
I = intermediate
S = sensitive
— = not done

Transformation. Avian *E. coli* Av was successfully transformed with pGOB18 by electroporation. This was confirmed by changes in antibiotic resistance profiles (Table 1) and plasmid screen profiles.

Conjugation studies. Escherichia coli AvGOB18 did not conjugate and pass pGOB18 to *E. coli* HB101, *E. coli* MC4100, or *E. coli* SK8203. In the positive control study *E. coli* V-2 conjugated with *E. coli* SK8203 and transferred $St^r$ at frequency of $Log_{10}$ 3.96 (Table 1). *Escherichia coli* V-2 was not reacted with *E. coli* HB101 and *E. coli* MC4100 because of similar antibiotic resistance profiles. Therefore, *E. coli* AvGOB18 is non-conjugative.

Colicin-like activity. *Escherichia coli* AvGOBI8 inhibited *Escherichia coli* Av, *E. coli* V-1, *E. coli* V-2, *E. coli* V-3, *E. coli* 0157:H7 (7 strains), *Salmonella typhimurium, S. enteriditis,*

*S. Heidelberg, S. infantis, S. typhimurium* (C), *S. kentucky,* and

*S. senftenberg. Escherichia coli* AvGOB18 did not inhibit *Escherichia coli* V-4, *Campylobacter jejuni,* or *Listeria monocytogenes.*

Survival of *E. coli* AvBOG18 in sterile tap and deionized water at 25 C. and 37 C. Survival of *E. coli* AvGOB18 in sterile deionized and tap water is shown in FIG. 1 and Table 4. Reisolates were positive for inhibition of *Salmonella typhimurium* 1769 as determined by the colicin-assay (Table 5).

Type f1 fimbriae and motility. *Escherichia coli* MC4100+ pGOB18 was non-motile and lacked type F1 fimbriae. *Escherichia coli* Av was non-motile and gave a weak positive reaction on the yeast agglutination test (type F1 fimbriae). *Escherichia coli* AvGOB18 was motile and gave a strong positive reaction on the yeast agglutination test.

In Vivo Bird Studies

I. Results of Bird studies #1 are shown in Table 2 below and FIG. 2. Birds housed in Horsfal Units.

TABLE 2

|  | Weeks | | | |
|---|---|---|---|---|
| Groups | 1 | 2 | 3 | 4 |
| Counts in $Log_{10}$ CFU/gram intestine | | | | |
| 1. Sal control | | | | |
| S. typh. 1769 | 5.33 | 4.63 | 2.54 | 2.39 |
| 2. E. coli AvGOB18 oral control | | | | |
| AvGOB18 | 0 | 0 | 0 | 0 |
| 3. E. coli AvGOB18 oral + Salmonella | | | | |
| AvGOB18 | 1.09 | 1.42 | 0 | 0 |
| S. typh. 1769 | 6.13 | 4.52 | 2.56 | 2.84 |
| 4. E. coli AvGOB18 in water + Salmonella | | | | |
| AvGOB 18 | 3.91 | 4.69 | 2.89 | 2.14 |
| S. typh. 1769 | 3.76 | 2.99 | 2.66 | 0.35 |

A. Reisolations from intestines were all positive for inhibition of *Salmonella typhimurium* 1769 in colicin-assay.
B. *Escherichia coli* AvGOB18 reisolated from intestinal tracts was immune to effects of *Salmonella typhimurium* 1769.

II. Results of Bird Study #2 are shown in Table 3 below and FIG. 3. Birds were housed in floor pens.

TABLE 3

|  | Weeks | | | |
|---|---|---|---|---|
| Groups | 1 | 2 | 3 | 4 |
| Counts in $Lot_{10}$ CFU/gram intestine | | | | |
| 1. Sal control | 3.28 | 3.99 | 2.63 | 2.31 |
| 2. E. coli AvGOB18 in water + Salmonella | | | | |
| AvGOB18 | 3.38 | 2.18 | 2.78 | 1.86 |
| S. typh. 1769 | 3.13 | 2.98 | 0 | 0.70 |

A. Reisolations from intestines were all positive for inhibition of *Salmonella typhimurium* 1769.
B. Reisolation from waters in floor pens:
*E. coli* AvGOB18, $Log_{10}$ 5.56 CFU/ml water, inhibitory to *Salmonella typhimurium* 1769.
C. *Escherichia coli* AvGOB18 reisolated from intestinal tracts was immune to effects of *Salmonella typhimurium* 1769.

TABLE 4

Survival of mutants in sterile deionized and tap water.

|  | Days | | | | | |
|---|---|---|---|---|---|---|
|  | 0 | 6 | 12 | 18 | 24 | 30 |
| *E. coli* GOB18 Counts in $Log_{10}$ CFU/ml water. | | | | | | |
| Deionized 25C | 6.7 | 8.0 | 8.1 | 7.7 | 8.0 | 7.7 |
| Tap 25C | 6.9 | 8.4 | 8.1 | 8.2 | 8.2 | 7.6 |

TABLE 4-continued

Survival of mutants in sterile deionized and tap water.

| | Days | | | | | |
|---|---|---|---|---|---|---|
| | 0 | 6 | 12 | 18 | 24 | 30 |
| Dionized 37C | 6.9 | 6.6 | 6.5 | 6.4 | 6.7 | 5.0 |
| Tap 37C | 6.9 | 6.1 | 5.8 | 6.1 | 5.7 | 5.3 |

TABLE 5

*Escherichia coli* AvGOB18 reisolated from water samples showing no zone of inhibition to *Salmonella typhimurium* 1769.

| Days | D 25C | T 25C | D 37C | T 37C |
|---|---|---|---|---|
| 3 | | | | |
| 6 | | | | X |
| 9 | | | | X |
| 12 | | | X | X |
| 15 | | | X | X |
| 18 | | | X | X |
| 21 | | | X | X |
| 24 | | | X | |
| 27 | | | X | |
| 30 | | | X | X |

D = sterile deionized water
T = sterile tap water
X = no zone of inhibition in colicin assay
Reisolation of non-Salmonella-inhibitory *E. coli* AvNZ5 varied with time, but at 37C the lose of inhibitory function was more evident.

CONCLUSIONS

In Vitro

*Escherichia coli* AvGOB18 produced a colicin-like peptide.

*E. coli* AvGOB18 inhibited 7 Salmonella serotypes commonly associated with poultry, 7 strains of *E. coli* 0157:H7, and 4 isolates of avian *E. coli* (3 associated with colibacillosis and 1 avirulent).

*E. coli* AvGOB18 did not inhibit an avian *E. coli* isolate, 3 serotypes of *Listeria monocytogenes*, or 1 isolate of *Campylobacter jejuni.*

*E. coli* AvGOBI8 was non-conjugative.

*E. coli* AvGOB18 survived in water at 25 C. and 37 C.

*E. coli* AvGOB18 was recovered from waters and birds and inhibited *Salmonella typhimurium* 1769.

In Vivo

*E. coli* AvGOB18 did not colonize the intestinal tract of broiler chicks when given as a single oral dose.

*E. coli* AvGOB18 significantly reduced the numbers of *Salmonella typhimurium* in the intestinal tracts of chickens, when the mutant *E. coli* was administered in the water supply.

*E. Coli* AvGOB18 was deposited with the American Type Culture Collection 10801 University Blvd., Manassas, Va. 20110-2209, Sep. 30, 1997 and has ATCC accession number 202040.

We claim:

1. A microorganism in biologically pure culture for administration to a fowl, the microorganism being *E. coli* AvGOB18, said microorganism being an avian enteric microorganism strain non-pathogenic to the fowl, containing and replicating a non-transmissible plasmid having genetic determinants for Microcin 24, and having the Mcc24$^+$ phenotype.

* * * * *